(12) United States Patent
Da Silva et al.

(10) Patent No.: US 6,607,500 B2
(45) Date of Patent: Aug. 19, 2003

(54) INTEGRATED CAST AND MUSCLE STIMULATION SYSTEM

(75) Inventors: Luiz B. Da Silva, Danville, CA (US); Michael R. Weber, Tampa, FL (US); David I. Blatt, Margate, FL (US); Jeffrey S. Mannheimer, Newton, PA (US)

(73) Assignee: Cyclotec Advanced Medical Technologies, Inc., Lauderhill, FL (US)

( * ) Notice: Subject to any disclaimer, the term of this patent is extended or adjusted under 35 U.S.C. 154(b) by 0 days.

(21) Appl. No.: 09/853,440

(22) Filed: May 10, 2001

(65) Prior Publication Data

US 2002/0016618 A1 Feb. 7, 2002

Related U.S. Application Data

(63) Continuation-in-part of application No. 09/350,426, filed on Jul. 8, 1999, now Pat. No. 6,445,955.

(51) Int. Cl.[7] .............................. A61F 5/01; A61N 1/18
(52) U.S. Cl. .............................. 602/2; 607/51; 607/115; 607/149; 600/386; 206/438
(58) Field of Search ................... 602/2, 60–62; 607/46, 48, 49, 50, 51, 52, 115, 149, 36; 600/386, 393; 206/438, 440

(56) References Cited

U.S. PATENT DOCUMENTS

| | | | | |
|---|---|---|---|---|
| 3,683,903 A | * | 8/1972 | Fox et al. | 602/7 |
| 3,893,462 A | * | 7/1975 | Manning | 600/13 |
| 4,509,520 A | * | 4/1985 | Dugot | 607/52 |
| 4,535,779 A | * | 8/1985 | Ober | 600/384 |
| 4,549,547 A | * | 10/1985 | Brighton et al. | 607/51 |
| 4,574,809 A | * | 3/1986 | Talish et al. | 600/13 |
| 4,583,550 A | * | 4/1986 | Montalbano et al. | 600/384 |
| 4,727,865 A | * | 3/1988 | Hill-Byrne | 24/68 SK |
| 4,729,377 A | * | 3/1988 | Granek et al. | 600/382 |

* cited by examiner

Primary Examiner—Kennedy Schaetzle
(74) Attorney, Agent, or Firm—John P. Wooldridge

(57) ABSTRACT

The present invention is a device that allows electrical stimulation to an anatomical site that is covered by a cast. The electrode is applied to achieve a desired physiological response (e.g., bone growth), treatment of pain, or the prevention of muscle atrophy.

21 Claims, 3 Drawing Sheets

INTEGRATED CAST AND MUSCLE STIMULATION SYSTEM

This is a continuation-in-part of U.S. patent application Ser. No. 09/350,426, titled "Miniature Wireless Transcutaneous Neuro Or Muscular-Stimulation Unit" filed Jul. 8, 1999, now U.S. Pat. No. 6,445,955, and incorporated herein by reference.

BACKGROUND OF THE INVENTION

1. Field of the Invention

The present invention relates to an integrated cast and muscle stimulation system, and more particularly, it relates to a treatment electrode device that provides electric stimulation to an anatomical site that is covered by a cast.

2. Description of Related Art

Injuries to the musculoskeletal system (bones, joints, muscles, ligaments, tendons) or conditions like arthritis, and osteoporosis are the leading reason for patient visits to physicians' offices. Sprains or dislocations and fractures account for almost half of all musculoskeletal injuries. Fractures can occur in a number of ways. Most fractures are the result of trauma (e.g., falls, car accidents). Osteoporosis, a bone disease, makes bones fragile and easily broken. Overuse can result in stress fractures, which are common among athletes. Physicians treat fractures with plaster casts, fiberglass casts, cast-braces, splints, pins or other devices to hold the fracture in the correct position while the bone is healing. Depending on the extent of the injury a fracture can take from several weeks to several months to heal.

Fractures are painful, but the pain usually stops long before the fracture is strong enough to handle normal activity. Usually, when the bone is healed the muscles are weak from lack of use. A period of rehabilitation is necessary for function to return to normal and healing to be complete. Today, amazing results are being seen in the treatment of bone fractures and other bone diseases with the use of electrical stimulation.

In U.S. Pat. No. 4,583,550, issued Apr. 22, 1986, an invention is described which incorporates a covered access window into a conventional plaster cast. An electrode can be applied through the access window. This invention is limited in size/shape of the electrode. Also, the invention is described for use with conventional plaster casts.

There are disadvantages to any kind of "windowing" in a cast. While cast saws are generally quite safe, it is still possible for abrasions to occur during the procedure. The cutting away of an area on a harden cast can also result in structural weakness to the cast. It is often desirable to apply an electrode directly to the fracture site, which is also the least desirable place to cut a window into a cast.

In U.S. Pat. No. 4,535,779, issued Aug. 20, 1985, a device is described which incorporates a flange and collar assembly into a cast. The flange and collar assembly can be attached to an external electric stimulator. This invention is labor intensive as well as physically limiting to the patient when the electric stimulator is attached to the cast.

Therefore, there is a need for an improved device and method for applying electrical stimulation to an anatomical site, which is covered by a cast. The present invention provides a new and improved device for integrating a treatment electrode in a body cast. The invention is simple in construction, use, and maintains the structural integrity of the cast while permitting reliable electrical stimulation.

SUMMARY OF THE INVENTION

An object of the present invention is to provide a device and method for applying a treatment electrode to an anatomical site covered by a cast.

These and other objects will be apparent to those skilled in the art based on the teachings herein. Other objects and advantages of the present invention will become apparent from the following description and accompanying drawings.

The invention integrates a treatment electrode into a cast. The cast is molded around the limb to immobilize the fracture. Replaceable electrodes are positioned over the peripheral nerves of the musculature surrounding the fracture site and an electrical stimulation unit applies voltage pulses to the electrodes through buried electrical conductors. A variety of electrical pulse formats can be used to achieve a desired result.

An exemplary description is provided for treating a patient with the present invention. The electrodes are inserted into a port that is placed within the cast during the cast building phase. The physician first winds a layer of soft material 50 around the limb. A port structure is then placed at the appropriate anatomical site for stimulation. An electrical stimulation unit is inserted into the port and electrical pulses are applied to the nerves underlying the electrodes.

An alternative method for integrating the port with the cast is provided. In this embodiment, the port structure has an outer segment that perforates the cast outer layers as they are wound around the affected area. After the cast has dried and set the outer segment is cut or snapped off exposing the port.

In an alternative embodiment the port structure is integrated with a soft material bottom layer that has a central hole. This embodiment would be applied to the skin before the soft material layer 50 is wound over the skin. The advantage of this approach is that it eliminates the need for pulling out or cutting out the soft material within the port aperture to expose the skin.

The electrode port structure allows the placement of both an electrode module and a restraint module. In order to prevent skin from herniating into the port, either an electrode module or restraint module should be placed within the port at all times.

The electrode module consists of a conductive layer that enables current to flow from the stimulator into the tissue. An electrical conductor connects the conductive layer to a conductive pad that makes contact with conductors when the electrode module is inserted into the port.

The restraint module is designed to have a total thickness that is comparable to the cast and port assembly. The bottom layer of the restraint module is made of a soft material. A flip top actuates pegs that lock into peg holes to hold the restraint module in place. An alternate o-ring design is provided for securing the restraint module.

BRIEF DESCRIPTION OF THE DRAWINGS

The accompanying drawings, which are incorporated into and form part of this disclosure, illustrate embodiments of the invention and together with the description, serve to explain the principles of the invention.

DETAILED DESCRIPTION OF THE INVENTION

Figure 1A:
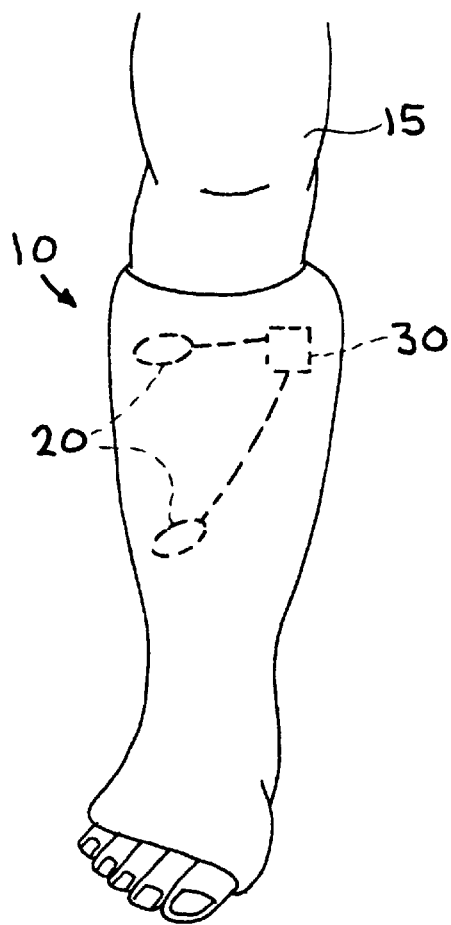
FIGS. 1A and 1B show a leg with a cast having an integrated muscle stimulation system.
Figure 1B:
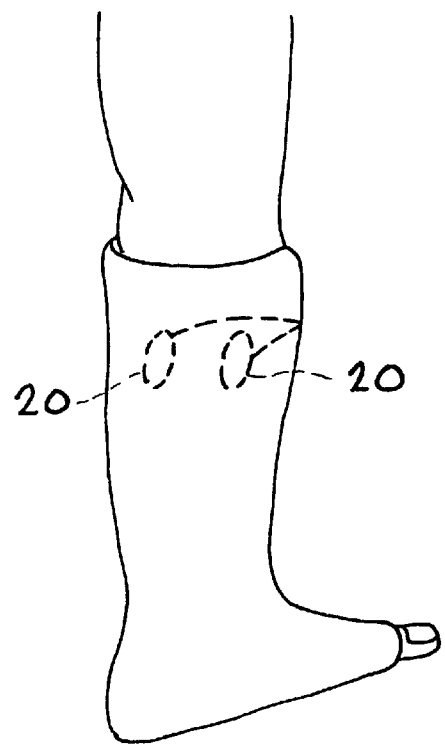

An embodiment of the present invention integrates a treatment electrode into a cast. FIG. 1 shows an illustration of the key components of the integrated cast and muscle stimulation system, as it would be used for a lower leg fracture. The cast 10 is molded around the lower leg 15 to immobilize the fracture. Replaceable electrodes 20 are positioned over superficial aspects of the peripheral nerves innervating the musculature surrounding the fracture site. An electrical stimulation unit 30 applies voltage pulses to the electrodes through buried electrical conductors 25. The electrical stimulation unit is similar to that previously described in U.S. Pat. No. 4,398,545 dated Aug. 16, 1983, incorporated herein by reference. A variety of electrical pulse formats can be used to block or control pain, increase circulation and/or exercise muscles.

Figure 2B:
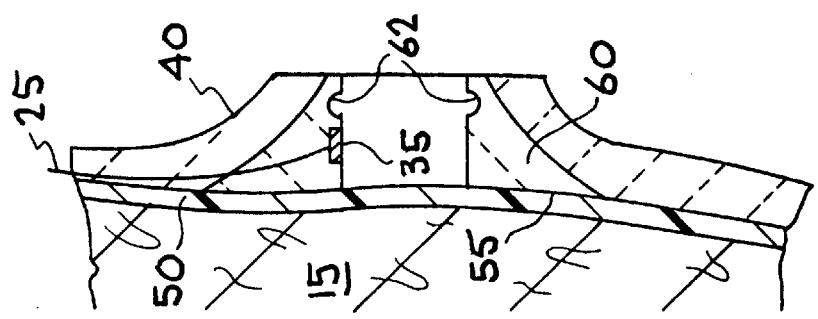
FIGS. 2A and 2B show a cross sectional view of how the port is integrated into the cast.
Figure 2A:
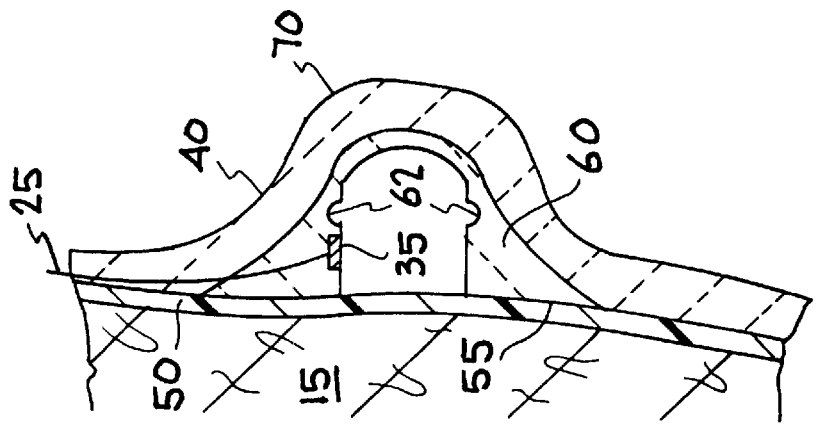

The replaceable electrodes 20 are inserted into a prepared port that is placed within the cast during the cast building phase. FIGS. 2A and 2B illustrate embodiments of how the port is integrated into the cast. First the physician winds a layer of soft material 50 (e.g., cotton, foam, etc.) around the skin (e.g., lower leg 15) covering the broken bone. A special port structure 60 is then placed at the appropriate anatomical site for stimulation. The bottom surface of the lower section 55 could be adhesive to prevent the port structure from moving. The physician next applies the cast outer layers 40 that cover the port structure 60 and form a raised region 70 (FIG. 2A). The electrical conductor 25 connects to a conductive pad 35 that is exposed at the internal surface of the port. An indentation 62 is used to capture the electrode or restraint module. After the cast has dried and is rigid a special saw is used to cut out the raised region producing a port as shown in FIG. 2B. The soft material 50 within the port structure can then be removed to expose the skin. The upper surface of the lower section 55 can be treated and coated with a primer to ensure bonding with the cast outer coat 40.

Figure 3B:
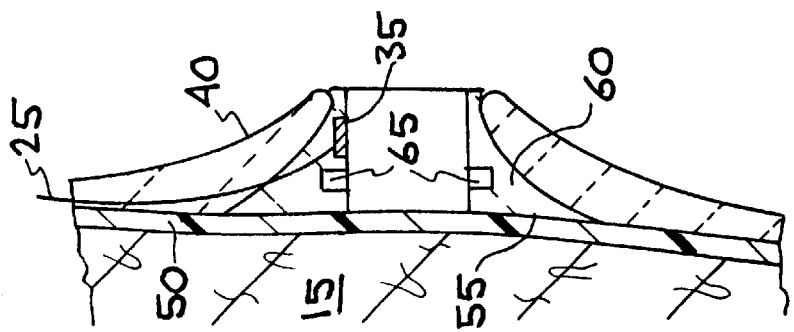
FIGS. 3A and 3B show a cross sectional view of how the port is integrated into the cast in an alternative embodiment.
Figure 3A:
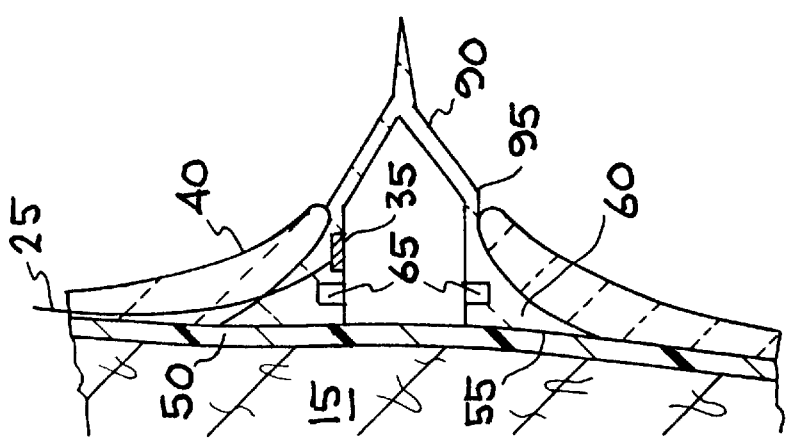

An alternative method for integrating the port with the cast is shown in FIGS. 3A and 3B. The port structure 60 has an outer segment 90 that perforates the cast outer layers 40 as they are wound around the affected area. The physician ensures that the outer layers are pushed beyond the lip 95. After the cast has dried and set the outer segment 90 is cut or snapped off exposing the port as shown in FIG. 3B. The port structure 60 is made of plastic in one embodiment. The lower segment 55 is made of soft material (e.g., polyurethane, silicone, fiberglass) to reduce the possibility of irritation to the patient. In addition, the lower segment 55 is made thin (<0.04") to prevent any excess pressure. The upper segment of the port structure is made of hard plastics, in one embodiment, to maintain shape and function over the one to three months of use. Radial peg holes 65 are used to locate and hold the electrode or restraint module in position. The electrical conductor 25 connects to a conductive pad 35 that is exposed at the internal surface of the port.

In an alternative embodiment the port structure is integrated with a soft material bottom layer that has a central hole. This embodiment would be applied to the skin before the soft material layer 50 is wound over the skin. The advantage of this approach is that it eliminates the need for pulling out or cutting out the soft material within the port aperture to expose the skin.

The electrode port structure 60 allows the placement of both an electrode module and a restraint module. In order to prevent skin hernia ting into the port it is important that either an electrode module or restraint module be in place within the port at all times. In normal use, the electrode module would only be used continuously for the first few days to block or reduce pain. After that time, electrode modules would only be applied several times a day for 10–20 minutes to stimulate the muscles and reduce muscular atrophy. Initially, the intensity of muscle stimulation would be low in order to prevent putting too much stress on the fracture. As the fracture heals, stimulation is increased to ensure that muscle tone is maintained during the one to three month healing period. The electrical stimulation unit can be preprogrammed to deliver a physician prescribed intensity pattern throughout the entire healing period. The device may also be used to relieve itching.

Figure 4:
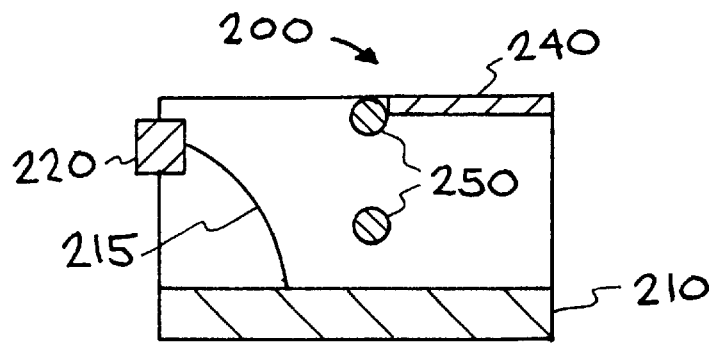
FIG. 4 shows a cross sectional view of the electrode module that is inserted into the port on the cast.

FIG. 4 shows a cross section through one embodiment of the electrode module 200. The electrode module consists of a conductive layer 210 that enables current to flow from the stimulator into the tissue. The conductive layer 210 can be a variety of different hygrogels and/or conductive adhesives or other conductive gels, or materials (e.g., Unipatch 'Permagel'™, Pepin 'PM-1000'™, Axelgaard 'Amgel'™, Ludlow RG63B'™). An electrical conductor 215 connects the conductive layer 210 to a conductive pad 220 that makes contact with pad 35 (FIGS. 2A–3B) when the electrode module is inserted into the port. A flip top 240 actuates the pegs 250 that lock into peg holes 65 (FIGS. 3a and 3B). Instead of pegs, the electrode module could us an o-ring design to lock within the indentation 62 (FIGS. 2A and 2B).

Figure 5:
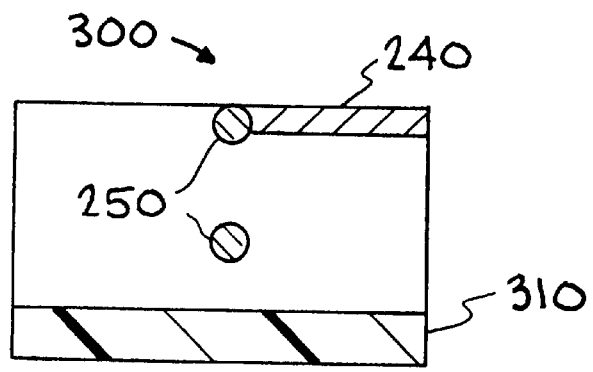
FIG. 5 shows a cross sectional view of the restraint module that is inserted into the port on the cast.

FIG. 5 shows a detailed cross section through one embodiment of the restraint module 300. This restraint module 300 is designed to have a total thickness that is comparable to the cast and port assembly. The bottom layer 310 of the restraint module is made of a soft material (similar to that used in building the cast layer 50 (FIGS. 2A–3B)). A flip top 240 actuates the pegs 250 that lock into peg holes 65 (FIGS. 3A and 3B). Instead of pegs, the electrode module could use an o-ring design to lock within the indentation 62 (FIGS. 2A and 2B). This restraint module is inserted into the port when the electrode module is removed. This prevents the skin from herniating into the open aperture.

Figure 6:
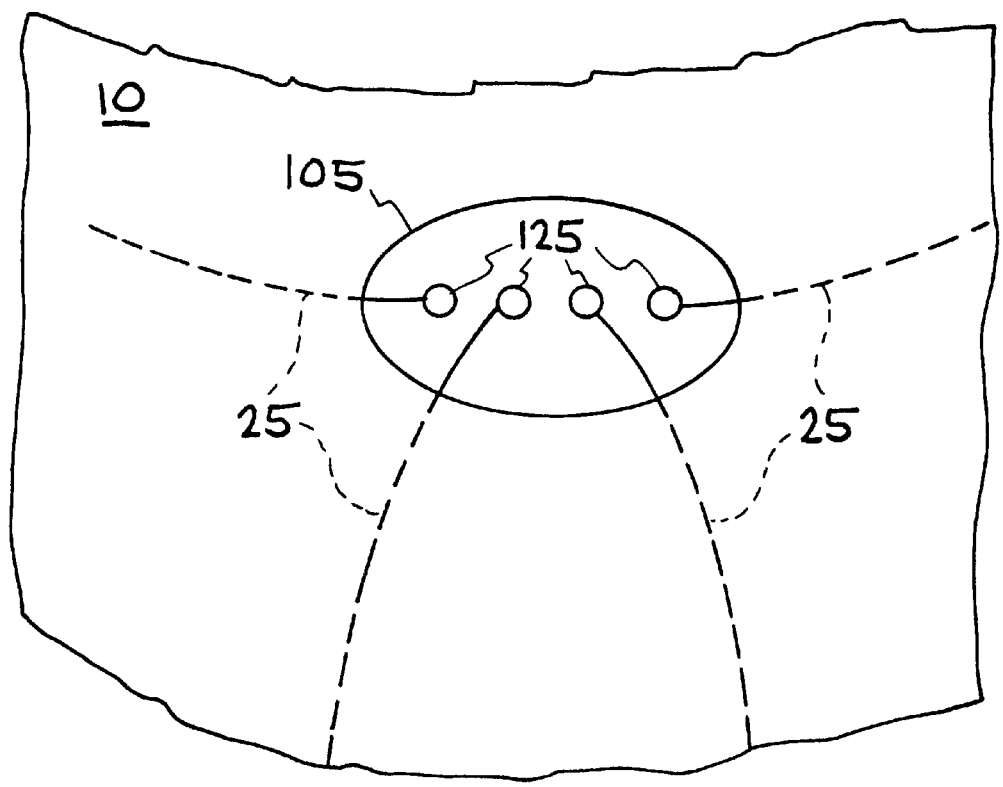
FIG. 6 shows a port for the electronic stimulation module that integrates into the cast and connects to the electrode ports.

FIG. 6 shows a port for the electronic stimulation module that integrates into the cast and connects to the electrode ports. The electrical conductors 25 that connect the port to the stimulator are protected from damage by the outer layers of the cast. The wires are available for connection to the electrical stimulator through a connector port 105 that integrates into the cast in a similar way to the electrode ports shown in FIGS. 2A–3B. The wires for the multiple electrode ports 25 connect to individual connector pins 125 as shown in FIG. 6. This connector port 105 is then used for both the electrical connection and to secure the electrical stimulator unit 30 (FIG. 1). In this way the user can remove the electrical stimulator unit when not in use. An optional plastic cap could be inserted to protect the connector pins 125.

Copending patent application titled "Two Part TENS Bandage" filed on the same day as this application is incorporated herein by reference.

The above descriptions and illustrations are only by way of example and are not to be taken as limiting the invention in any manner. One skilled in the art can substitute known equivalents for the structures and means described. The full scope and definition of the invention, therefore, is set forth in the following claims.

We claim:

1. An apparatus, comprising:

a cast;

a plurality of electrode ports integrated into said cast, wherein said electrode ports comprise means for holding an electrode module or a restraint module;

an electrical conductor connected to an electrode port of said plurality of electrode ports; and a stimulator port within said cast, wherein said stimulator port comprises means for containing an electrical stimulation unit (ESU) and for providing a conductive path between each said electrical conductor and said ESU.

2. The apparatus of claim 1, further comprising an ESU.

3. The apparatus of claim 2, wherein said ESU comprises a programmable memory.

4. The apparatus of claim 1, further comprising means for holding an ESU in said stimulator port and releasing said ESU from said stimulator port.

5. The apparatus of claim 1, wherein said electrode port comprises an adhesive surface.

6. The apparatus of claim 1, wherein said electrode port comprises an internal surface with an electrode port conductive pad for providing electrical connection between said electrode module and electrical stimulation unit (ESU), wherein said electrode port conductive pad is exposed at the internal surface of said electrode port.

7. The apparatus of claim 6, wherein said electrode module comprises:

a conductive layer that enables current to flow from said ESU stimulator into tissue;

an electrical conductor connected to said conductive layer; and an electrode module conductive pad that makes contact with said electrode port conductive pad when said electrode module is inserted into said electrode port.

8. The apparatus of claim 7, wherein said conductive layer comprises material selected from the group consisting of a hygrogel, a conductive adhesive, a conductive gel and a conductive material.

9. The apparatus of claim 7, wherein said conductive layer comprises a conductive gel.

10. The apparatus of claim 1, wherein said stimulator port comprises an indentation for capturing said ESU.

11. The apparatus of claim 1, wherein said eledrode port comprises an indentation for capturing said electrode or restraint module.

12. The apparatus of claim 1, wherein said electrode port comprises an outer segment for perforating a portion of said cast, wherein said outer segment may be cut or snapped off to expose said electrode port.

13. The apparatus of claim 12, wherein said electrode port comprises plastic.

14. The apparatus of claim 1, wherein said electrode port comprises a lower segment for placement near the skin of a patient, wherein said lower segment comprises a soft material to reduce the possibility of irritation to the patient.

15. The apparatus of claim 14, wherein said soft material is selected from the group consisting of polyurethane, silicone and fiberglass.

16. The apparatus of claim 1, wherein said electrode port comprises a lower segment for placement near the skin of a patient, wherein said lower portion is less than 0.04 inches thick to prevent any excess pressure.

17. The apparatus of claim 1, wherein said electrode port comprises an upper segment for placement away from the skin of a patient, wherein said upper segment comprises a hard plastic to maintain shape and function over the lifetime of the use of said apparatus.

18. The apparatus of claim 1, wherein said stimulator port comprises radial peg holes for locating and holding an ESU.

19. The apparatus of claim 1, wherein said electrode port comprises radial peg holes for locating and holding said electrode module or said restraint module in position.

20. The apparatus of claim 1, wherein said restraint module comprises a soft material.

21. A method for treating a patient, comprising:

forming a cast onto a limb of said patient;

integrating a plurality of electrode ports into said cast, wherein said electrode ports comprise means for removably restraining an electrode module;

providing an electrode module in at least two electrode ports;

providing a stimulator port within said cast for containing an electrical stimulation unit (ESU) and for providing a conductive path between each said electrode port and said ESU, wherein said stimulator port comprise means for removably restraining an ESU;

securing an ESU within said stimulator port; and energizing at least two electrode modules.

* * * * *